United States Patent
Richart

(10) Patent No.: US 11,806,172 B2
(45) Date of Patent: Nov. 7, 2023

(54) DEVICE FOR PACKAGING AN OBJECT, ASSEMBLY AND CORRESPONDING EXTRACTION METHOD

(71) Applicant: SELENIUM MEDICAL, La Rochelle (FR)

(72) Inventor: Olivier Richart, Le Bois Plage en Re (FR)

(73) Assignee: SELENIUM MEDICAL, La Rochelle (FR)

( * ) Notice: Subject to any disclaimer, the term of this patent is extended or adjusted under 35 U.S.C. 154(b) by 0 days.

(21) Appl. No.: 16/637,334

(22) PCT Filed: Aug. 7, 2018

(86) PCT No.: PCT/FR2018/052027
§ 371 (c)(1),
(2) Date: Feb. 7, 2020

(87) PCT Pub. No.: WO2019/030451
PCT Pub. Date: Feb. 14, 2019

(65) Prior Publication Data
US 2022/0061948 A1    Mar. 3, 2022

(30) Foreign Application Priority Data

Aug. 10, 2017 (FR) ...................... 17 57632

(51) Int. Cl.
*A61B 50/30* (2016.01)
*A61B 50/00* (2016.01)

(52) U.S. Cl.
CPC ...... *A61B 50/30* (2016.02); *A61B 2050/0056* (2016.02)

(58) Field of Classification Search
CPC ........................ A61B 50/30; A61B 2050/0056
(Continued)

(56) References Cited

U.S. PATENT DOCUMENTS

| 10,398,523 B2 * | 9/2019 | Roesler ................. A61C 8/0087 |
| 2003/0221977 A1 * | 12/2003 | Kumar ................. A61C 8/0087 |
| | | 206/63.5 |

(Continued)

FOREIGN PATENT DOCUMENTS

| DE | 10146905 | 7/2003 | |
| DE | 10146905 A1 * | 7/2003 | ............. A61B 50/30 |

(Continued)

OTHER PUBLICATIONS

Search Report dated Apr. 20, 2018.
International Search Report dated Mar. 29, 2019.

*Primary Examiner* — J. Gregory Pickett
*Assistant Examiner* — Sanjidul Islam
(74) *Attorney, Agent, or Firm* — Sofer & Haroun, LLP

(57) ABSTRACT

The invention relates to a device for packaging an object, comprising: a main hollow body (100), a closure element (101), and a support (110) housed inside the main hollow body (100), said support being configured to receive an object (150), such as a medical implant. The support comprises a seat having an axial through-hole designed to allow part (170) of the object (150) to extend below the seat, while another part (160) of the object (150) bears on the seat. The packaging device is configured to limit or block the rotation of the support (110) relative to the main hollow body (100) about the axis of the through-hole in the seat. The support (110) is designed to limit or block the rotation of at least part of the object (150) about said axis, whereby the object (150) can move freely out of the main hollow body (100) when the closure element (101) is open. The invention also relates to a corresponding extraction method.

15 Claims, 6 Drawing Sheets

(58) Field of Classification Search
   USPC .......................................... 206/438; 606/301
   See application file for complete search history.

(56) References Cited

U.S. PATENT DOCUMENTS

| | | |
|---|---|---|
| 2004/0112781 A1 | 6/2004 | Hofverberg et al. |
| 2008/0257760 A1 | 10/2008 | Hanada et al. |
| 2011/0247947 A1 | 10/2011 | Nihei et al. |
| 2017/0095308 A1 | 4/2017 | Roesler et al. |

FOREIGN PATENT DOCUMENTS

| | | | | |
|---|---|---|---|---|
| DE | 202014100438 | | 4/2014 | |
| JP | 2008 125982 A | | 6/2008 | |
| JP | 2008125982 A | * | 6/2008 | ........... A61C 8/0087 |
| KR | 2013 0055421 | | 5/2013 | |
| KR | 2013 0055426 | | 5/2013 | |
| WO | 2018/009401 | | 1/2018 | |
| WO | WO-2018009401 A | * | 1/2018 | ............. A61B 17/70 |

\* cited by examiner

US 11,806,172 B2

DEVICE FOR PACKAGING AN OBJECT, ASSEMBLY AND CORRESPONDING EXTRACTION METHOD

RELATED APPLICATION

This application is a National Phase of PCT/FR2018/052027 filed on Aug. 7, 2018 which in turn claims the benefit of priority from French Patent Application No. 17 57632 filed on Aug. 10, 2017, the entirety of which are incorporated by reference.

FIELD OF THE INVENTION

The present invention relates in general to the packaging of objects and, in particular, the packaging of a medical implant.

PRIOR ART

Packaging a medical implant by positioning it inside a tube closed by a stopper is known from the prior art. In order to remove the implant, the operator uses an instrument which engages into the tube to connect the implant to said instrument and extract the implant from the tube.

However, it is found that the implant may remain stuck in the tube, and this is a source of complications for the operator who wishes to be able to extract the implant quickly and easily. Furthermore, there is a risk that the tube and/or the implant stuck in the tube may become damaged during forcible extraction of the implant.

Packaging for objects are also known from documents EP2377489 A1, EP1985257 A1, JP2008125982 A, KR20130055426 A and KR20130055421 A, EP3153128 A1 and WO 2018009401.

It is nevertheless desirable to offer a novel object packaging device that can be used reliably, notably allowing a user to unpackage the object easily, with a reduced risk of the object becoming impaired or contaminated. It is desirable for the user to be able to extract the object from said packaging device easily.

SUMMARY OF THE INVENTION

To this end, one subject of the invention is a device for packaging an object, comprising:
  a main hollow body, such as a tube or a case,
  a closure element able with respect to the main hollow body to exhibit a closed configuration in which access to the opening of the main hollow body is limited or prevented, and an open configuration in which access to the opening of the main hollow body is free,
  characterized in that the packaging device also comprises a support housed inside the main hollow body, said support being configured to accept an object, such as a medical implant;
  and in that the support comprises a seat having a through-passage, said through-passage being configured to allow part of the object to extend below the seat, while another part of the object remains resting on the seat,
  said packaging device being configured to limit or block the rotation of the support with respect to the main hollow body about the axis of the through-passage of the seat,
  and in that the support is configured to limit or block the rotation of at least part of the object about the axis of the through-passage of the seat, the object being freely movable from the main hollow body when the closure element is in the open configuration.

Such a design of packaging device makes it possible to enjoy a function whereby the object housed in the main hollow body via the support is prevented from rotating with respect to the support and with respect to the main hollow body, this allowing the operator to couple the instrument to the object quickly by a rotational coupling of part of the instrument and a corresponding part of the object without the object rotating freely in the main hollow body under the effect of the rotational movement of the instrument. Furthermore, the fact that the object can be moved freely in the axial direction toward the opening of the main hollow body allows the operator, who has coupled his instrument to the object, to extract the object from the main hollow body quickly and simply. Furthermore, the operator also retains the possibility—notably in an emergency—to simply slide the object out of the main hollow body by inclining the latter downward.

As the support has an axial through-passage, the object can be suspended with part resting axially in the support (on the seat of the support) and part extending through the axial through-passage (when the opening of the main hollow body is oriented upward), thus allowing the user to visualize the length of the object.

In particular, in the case of a pedicle screw, provision may be made for the tulip, which is housed in the seat of the support, to extend partly beyond the support and for the screw part to extend through the axial passage under the seat, this allowing the user quickly to determine what kind of object it is, and the length thereof.

The packaging device may also comprise one or more of the following features considered in any technically permissible combination.

According to one particular aspect, said main hollow body is closed at one end and open at another end to define the object outlet opening.

The axis of the passage passing through the seat about which rotation of the object with respect to the support is limited or prevented, may also be defined as being an axis parallel to or coincident with the normal to the opening face of the main hollow body (axis of the opening) or else the normal to the bottom of the main hollow body. When the main hollow body is elongate this axis is parallel to or coincident with the longitudinal axis of said main hollow body.

The support thus forms an anti-rotation stop preventing the object from rotating about the axis of the passage passing through the seat (which also corresponds to the axis of introduction/extraction) of the object into/from the main hollow body.

The, for example, peripheral, interior wall of the seat intended to accept the upper part or head of the object does not exhibit symmetry of revolution. According to one particular aspect, the, for example peripheral, interior wall of the seat is configured to come into contact with at least part of the, for example peripheral, exterior wall of the head of the object when the head of the object is in the state supported by the seat so as to limit or block the rotation of the head of the object with respect to the seat.

According to one particular aspect, the limiting or the blocking of the rotation of the head of the object with respect to the seat is obtained by at least partial collaboration of shapes between the head of the object and the seat.

The object is not wedged in the seat or in the main hollow body in the sense that, at least when the end opening of the main hollow body is in the blocked-off state, the object is able to slide axially, notably so as to be able to be extracted or to escape from the hollow body under the effect of gravity by inclining the hollow body in such a way as to orient the head of the object downward.

Said support may be attached inside the main hollow body. As an alternative, said support may be formed as a single piece with said hollow body. In other words, the main hollow body and the support may be monobloc.

In one embodiment whereby the support is attached, it has an exterior shape which does not exhibit symmetry of revolution. As the support is in contact over at least certain parts of its, for example peripheral, exterior surface with the, for example peripheral, interior surface of the main hollow body, the support is therefore, because of its exterior shape, limited and/or blocked in terms of rotation with respect to the hollow body about the axis of the passage passing through the seat.

Such a design of the support being attached inside the hollow body offers the possibility to use the one same model of hollow body for different applications and/or the one same model of support for different hollow bodies, thus making it possible to benefit from a high degree of industrial flexibility.

According to one advantageous feature of the invention, because the closure element is hollow, the object extends partly projecting from the opening of the main hollow body into the closure element when the closure element is in the closed configuration.

In instances in which the object, particularly its head, projects out from the opening of the main hollow body, an operator can easily extract the object, preferably using a tool, so as to limit the risk of contamination of the object where appropriate.

According to one advantageous feature of the invention, the support comprises a top wall of which the internal face is configured in such a way as, in collaboration with the external face of the object, to limit or block the rotation of said at least part of the object about the axis of the through-passage of the seat.

According to one advantageous feature of the invention, the support also comprises a bottom wall delimiting an axial passage in which part of said object is able to extend when said object is in the state in which it is resting on the seat.

According to one advantageous feature of the invention, the bottom wall of the support has an opposite end to the seat which comes into contact with or the immediate vicinity of the bottom of the main hollow body.

According to one advantageous feature of the invention, the support is configured to limit or block an angular movement of the part of the object which extends into the passage delimited by the bottom wall of the support.

The angular movement is a movement, for example of pendular type, about an axis orthogonal to the axis of the passage passing through the seat.

According to one advantageous feature of the invention, the external face of the support comprises at least one planar part facing a planar part of the internal face of the main hollow body so as to limit or block the rotation of the support with respect to the main hollow body about the axis of the through-passage of the seat.

According to one advantageous feature of the invention, the packaging device comprises a retaining element which is housed between the closure element and the object so as to block or limit the sliding of the object toward the opening of the main hollow body.

According to one advantageous feature of the invention, the bottom wall of the support comprises at least one tab, preferably two diametrically opposed longitudinal tabs, of which at least part extends toward the axis of the through-passage of the seat so as to make it possible to limit or block the angular travel of the part of the object that extends in the space delimited by the bottom wall.

According to one advantageous feature of the invention, the support comprises two half-shells that can be assembled with one another by snap-fastening.

According to one advantageous feature of the invention, the main hollow body is translucent or transparent.

According to one advantageous feature of the invention, the top wall of the support has two diametrically opposed openings which define a reference for the orientation of the object with respect to the support when it is being introduced into the support.

These openings may take the form of slots.

The invention also relates to an assembly comprising a packaging device as described hereinabove, and said object.

According to one particular aspect, said object comprises a body, preferably a hollow body, called a tulip, which has a tapped thread or an external thread, the tulip being configured in such a way as to allow, when the closure element is in the open state, the use of an instrument having a complementary part able to engage with the tapped thread or the external thread of the tulip so as to extract the object from the main hollow body.

According to one particular aspect, the tulip has an upper opening which has a tapped thread with which a threaded element, usually referred to as a screw or a locking nut or alternatively an "end cap" is able to collaborate. The tapped thread of this upper opening can be used to collaborate with an external thread of the instrument.

According to one particular aspect, the object comprises a screw of which the head is coupled to the tulip with a ball-joint connection, or fixedly.

The invention also relates to a method for extracting the object of a packaging device as described hereinabove, said method comprising the following steps:
  opening the closure element so as to open the main hollow body;
  bringing a coupling part of an instrument into contact with a corresponding part of the object;
  coupling the instrument to the object by rotating the coupling part of the instrument about the axis of the through-passage of the seat;
  extracting the instrument and the object, coupled to the instrument, from the main hollow body.

BRIEF DESCRIPTION OF THE DRAWINGS

Further features and advantages of the invention will become further apparent from the following description, which is purely illustrative and nonlimiting and is to be read in connection with the attached drawings in which.

DETAILED DESCRIPTION

The concept of the invention is more fully described hereinafter with reference to the attached drawings, in which embodiments of the concept of the invention are shown. Similar numerals refer to similar elements across all the drawings. However, this concept of the invention can be implemented in numerous different forms and should not be interpreted as being limited to the embodiments set forth here. Rather, these embodiments are proposed in order for this description to be complete, and impart to those skilled in the art the extent of the concept of the invention. The extent of the invention is therefore defined by the attached claims.

Throughout the description, reference to "an embodiment" means that a functionality, a structure or a particular feature described in connection with an embodiment is included in at least one embodiment of the present invention. Thus, where the expression "in one embodiment" appears at various points throughout the description, this does not necessarily refer to the one same embodiment. Furthermore, the functionalities, the structures or the particular features may be combined in any suitable way in one or more embodiments. A feature presented in one embodiment may be applied, in isolation or in combination with one or more other features of this embodiment, to the other embodiments where this is technically appropriate.

With reference to the figures and as recalled hereinabove, the invention relates to a device for packaging an object.

In the example illustrated in FIGS. 1 to 6A, said main hollow body takes the form of a tube. According to one particular aspect, a stopper forming a closure element can be screwed onto the open end of the tube to close it. The stopper may or may not be hollow.

The main hollow body may be a body other than a tube. The main hollow body may take the form of a shell (lower shell) able to collaborate with another shell (upper shell) or lid forming said closure element (or stopper). The main hollow body may also be considered as a case, for example of blister type, having an opening, which may or may not be resealable, by the closure element as illustrated more particularly in FIGS. 7 and 7A. Provision may be made for the main hollow body to be resealable after opening, or not.

The main hollow body may have different shapes of cross section, for example oblong, circular, rectangular or square with rounded edges, etc.

The main hollow body and the closure element may take the form of two half-shells, of the type described in application WO2014188142 A1 or else in application WO2018078242A1, the content of each of these applications being incorporated by reference in its entirety into the present application.

In the example illustrated in the figures, said object is a medical implant, for example a pedicle screw.

Figures 5, 5A:
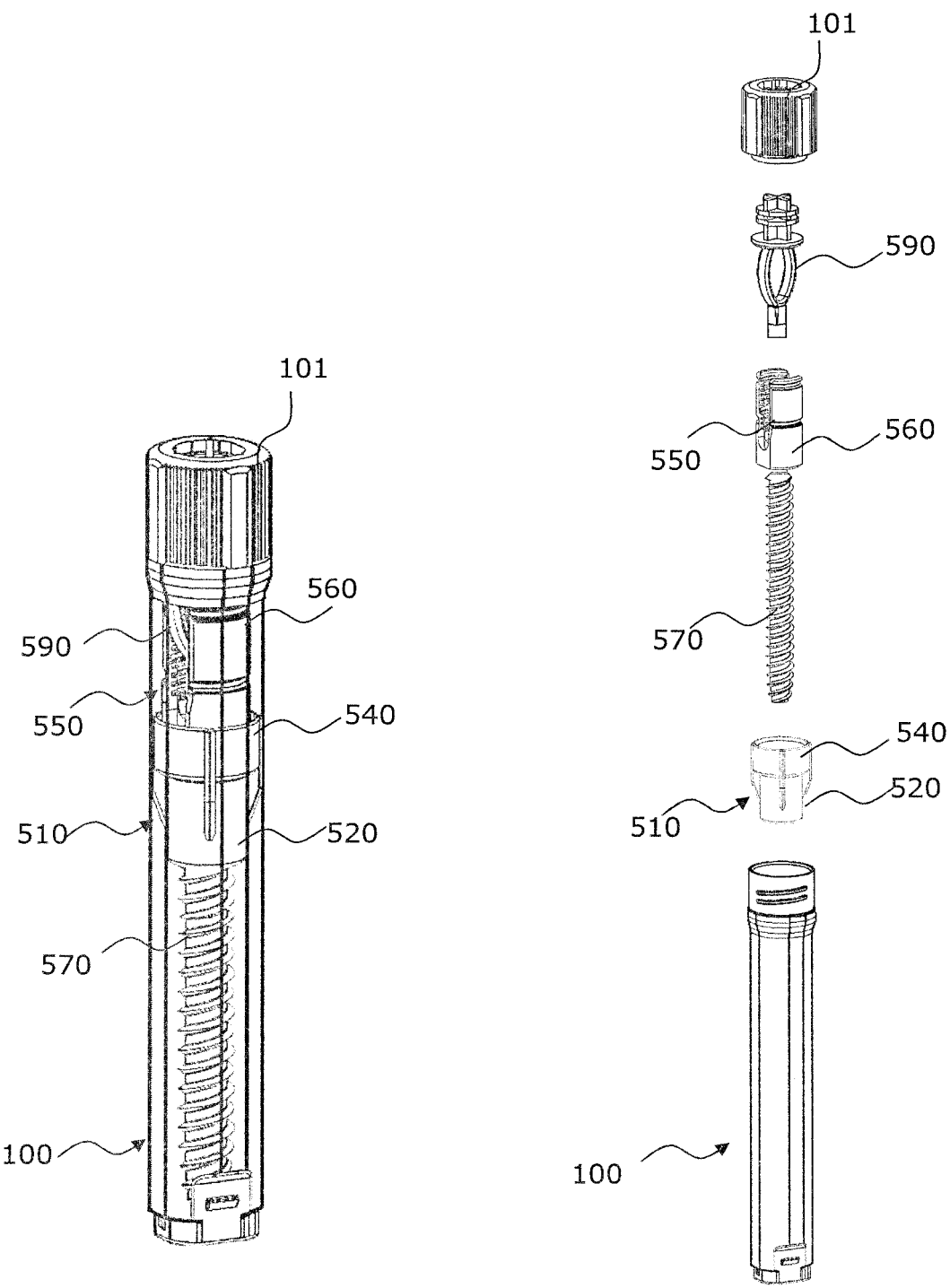
FIG. 5 is a perspective view of a packaging device according to a second embodiment of the invention.
FIG. 5A is an exploded view of the packaging device of FIG. 5.
Figures 6, 6A:
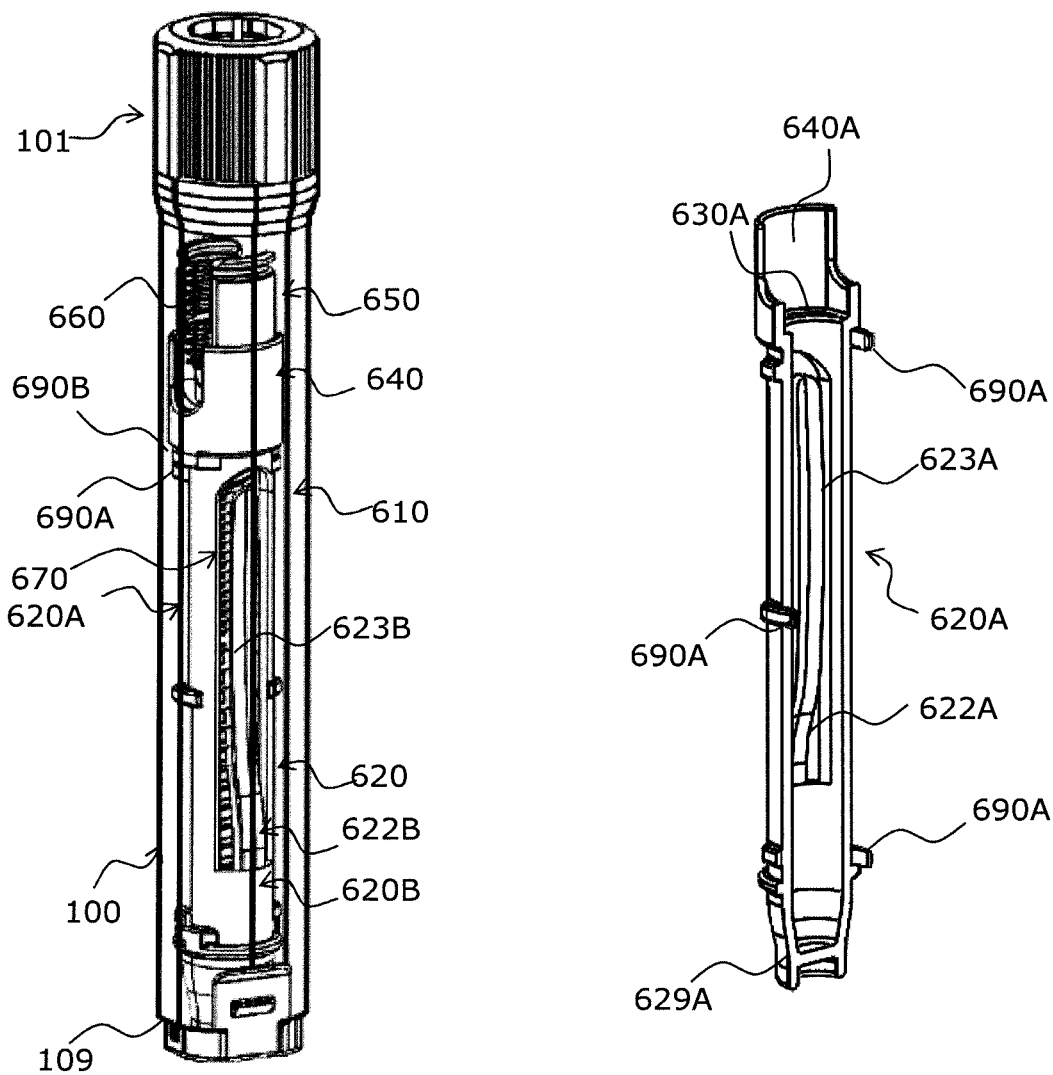
FIG. 6 is a perspective view of a packaging device according to a third embodiment of the invention.
FIG. 6A is a perspective view of a half-shell that forms part of the support included in the packaging device of FIG. 6.
Figure 7:
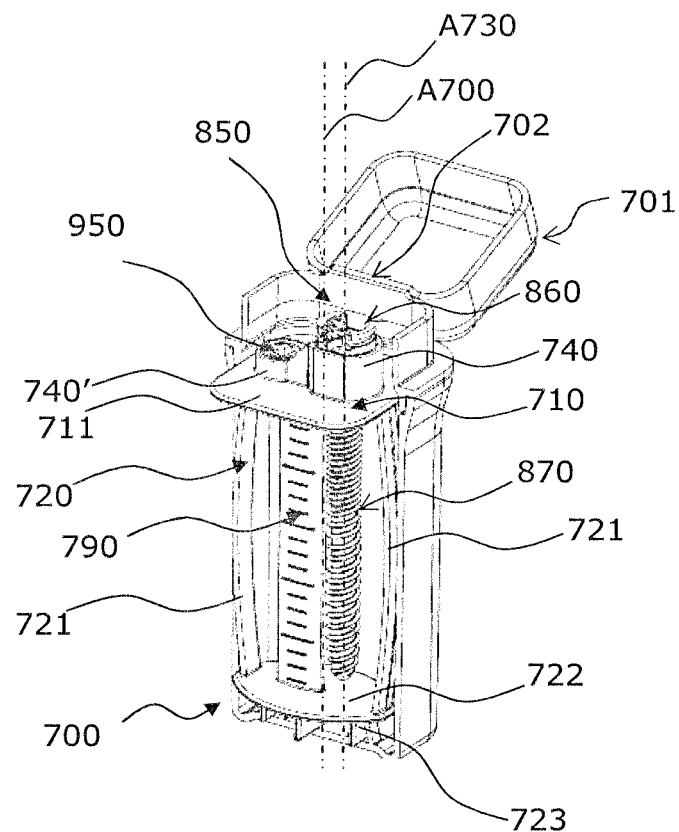
FIG. 7 is a perspective view of a packaging device according to a fourth embodiment of the invention, in the state in which two objects are housed in a main hollow body via a support also housed in the main hollow body, a lid connected to the main hollow body being in the open position, just half of the main hollow body being depicted.
Figure 7A:
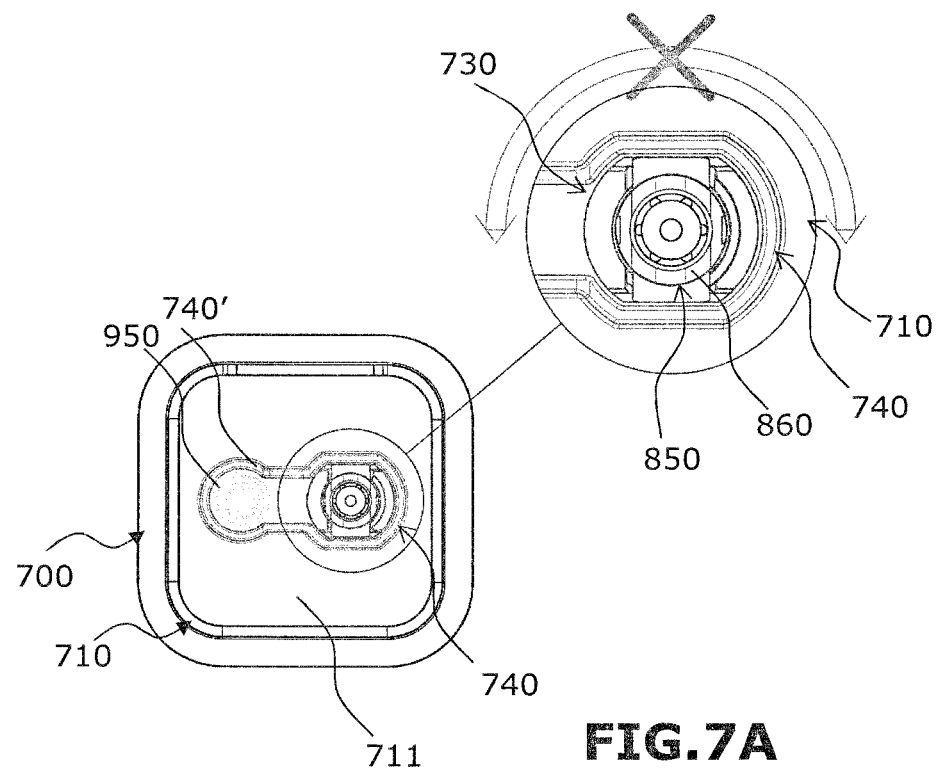
FIG. 7A is a view from above, accompanied by a detail view, showing one of the objects, for example a pedicle screw tulip, of the packaging device of FIG. 7, blocked from rotating with respect to the support.
Figure 7B:
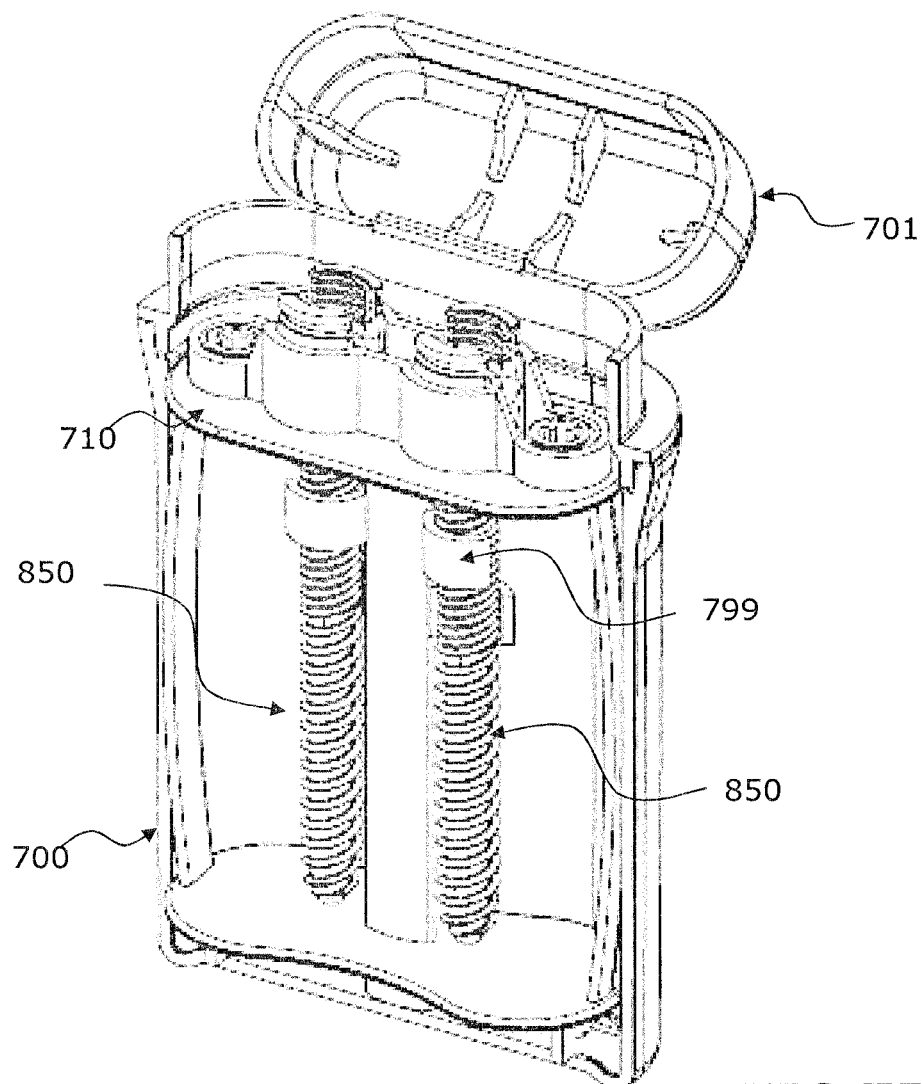
FIG. 7B is another embodiment of a packaging device according to the invention, a lid connected to the main hollow body being in the open position, just half of the main hollow body being depicted, and in which the support is able to house four objects, in this instance two pedicle screws, while preventing or limiting the rotation thereof, as well as two optional locking nuts.

The features set out in the examples of FIGS. 1 to 6A may be applied to embodiments for which the main hollow body is not a tube but some other element, such as a half-shell or case able to be closed by another half-shell or lid, as in the case of FIGS. 7, 7A and 7B.

Figure 1:
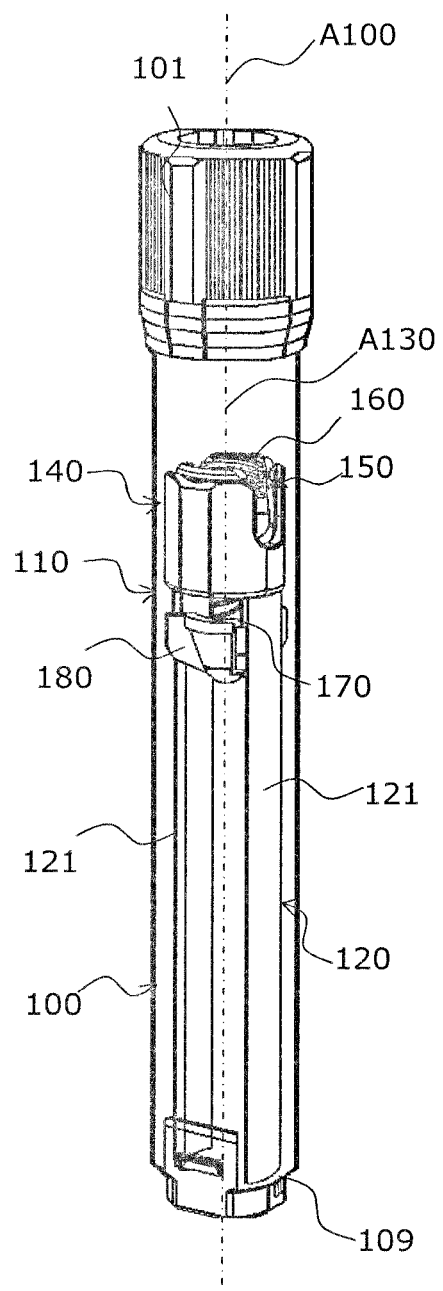
FIG. 1 is a perspective view of a packaging device according to a first embodiment of the invention, which contains a medical implant and of a support accommodating the medical implant.

In the embodiment of FIG. 1, the device comprises a tube 1 which has a longitudinal axis A100. A stopper 101 allows the opening of the tube 100 to be closed. Said tube 100 is closed at one end 109 and has an opening at the other end. The axis A100 corresponds to the axis via which the object enters/exits the tube via the opening, and to the longitudinal axis of the tube. The tube contains an object 150, such as a medical implant. According to one particular aspect, the tube 100 is translucent or transparent.

In the example illustrated in the figures, the object 150 is a medical implant which comprises a body, referred to as a tulip 160, and a screw 170 the head of which is coupled to the tulip 160.

The tulip 160 has an opening, referred to as the upper opening, oriented toward the opening of the tube 100 so as to make it possible, in the state in which the stopper 101 is being removed, to introduce into the tube 100 an instrument having a threaded part able to engage with a tapped thread 162 formed inside the tulip 160.

The head of the screw 170 is coupled to the tulip 160, with a ball-joint connection or fixedly. The head of the screw 170 has a socket 171 accessible from the upper opening of the tulip 160 so as to allow the operator, who has introduced an instrument into the tulip and coupled the tool to the tulip by collaboration between the external thread of part of the instrument and the tapped thread of the tulip, to actuate the instrument to engage an element of the instrument with the screw head.

Quite obviously, it would have been conceivable to have a tulip with a thread on the outside, namely an external thread, to collaborate with a complementary part of the instrument, this complementary part of the instrument corresponding to a thread on the inside, namely a tapped thread.

Such instruments are well known to those skilled in the art and will not be described in further detail hereinafter. For example, such instruments are marketed under the name Degenerative Spinal System EVEREST (registered trademark) by the company K2M, or else under the name MONTBLANC (registered trademark) by the company SPINEWAY, or under the name XIA 3 (registered trademark) by the company STRYKER spine, or else under the name CD HORIZON legacy (registered trademark) by the company MEDTRONIC SOFAMOR DANEK, or else under the name EXPEDIUM (registered trademark) by the company DEPUY SPINE, or else under the name KAPITOL or CREO (registered trademark) by the company GLOBUS MeDICAL, or else under the name SEQUOIA (registered trademark) by the company ZIMMER, or else under the name SILVERTONE (registered trademark) by the company BIOMET.

The following description is thus given in respect of, for example, an object formed by the medical implant 150, 550 or 650 or 850 depending on the embodiment, but the description of course applies to any other object configured to be housed in the support and of which the rotation with respect to the support is limited or blocked, while at the same time maintaining the possibility of being taken out of the tube freely when the stopper has been removed.

As illustrated in FIG. 1, the packaging device also comprises a support 110 housed inside the tube 100. According to one particular aspect, the support 110 is fully housed in the tube. Said support 110 is configured to accept the medical implant 150.

By accepting the medical implant 150, said support notably allows the medical implant 150 to be held in the tube away from the bottom of the tube. According to one particular aspect, the medical implant 150 is held in a given position along the tube.

The rotation of the support 110 with respect to the tube 100 about the longitudinal axis of the tube is limited or blocked. The other embodiments depicted, described hereinafter, also exhibit an anti-rotation function preventing the support from rotating with respect to the tube and an anti-rotation function preventing the implant from rotating with respect to the support.

Figure 2:
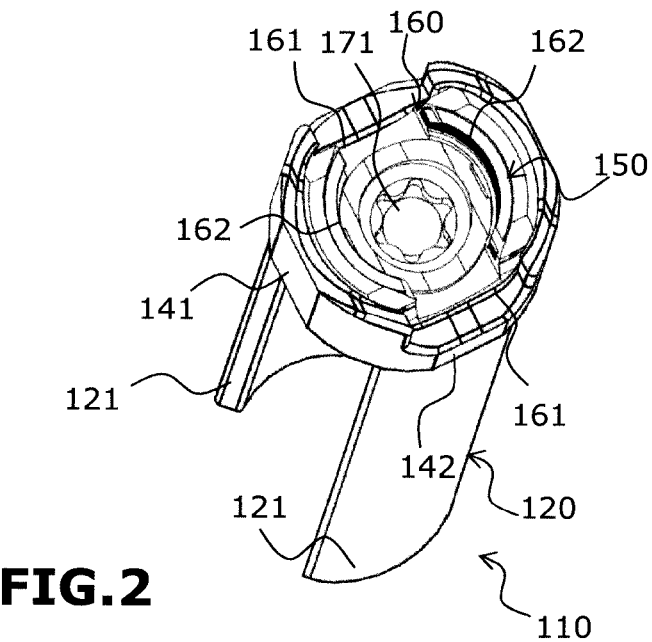
FIG. 2 is a perspective view of a support and of a medical implant housed in the support, said support and said medical implant being intended to be housed in a tube closed by a stopper to form or form part of a packaging device, for example in accordance with FIG. 1.
Figure 4:
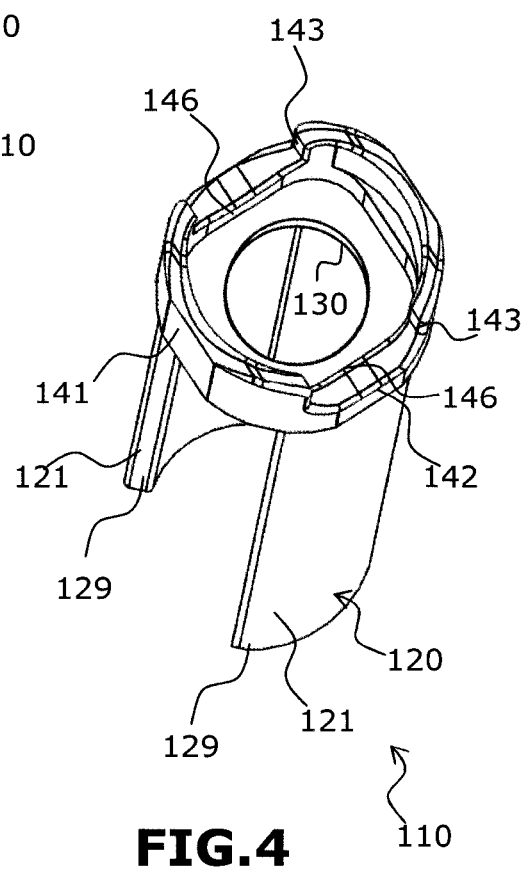
FIG. 4 is an isolated view of a support for example in accordance with the support of FIG. 2.

According to one particular aspect and as illustrated more particularly in FIG. 2 or 4, the external face of the support comprises at least one planar part 141, 142 intended to come to face a planar part of the internal face of the tube 100 so as to limit or block the rotation of the support 110 with respect to the tube 100 about the longitudinal axis of the tube.

According to one embodiment and as for example illustrated in FIG. 2 or 4, the support 110 has on its exterior face four planar parts 141, 142 distributed at 90° from one another about the axis of the passage delimited by the support which corresponds to the longitudinal axis of the tube when the support is in the state in which it is housed inside the tube.

The support 110 is also configured to limit or block the rotation of the medical implant 150, with respect to the support 110 and therefore with respect to the tube, about the longitudinal axis of the tube. The longitudinal axis of the tube more or less coincides with the axis of the passage delimited by the support 110 when the support is in the state in which it is housed inside the tube. Nevertheless, the medical implant 150 can still be moved freely in the axial direction out of the tube 100 when the stopper is removed from the tube.

What is meant by freely is that the object can be taken out of the tube once the stopper has been removed, without the need to inactivate any retention mechanism or to free the object. In other words, when the stopper is in the removed state, the object can easily and quickly be extracted from the tube, without being retained by the support or by the tube.

In particular, the object remains free to slide axially out of the tube 100 by inclining the tube by orienting its opening downward with the stopper 101 in the removed state.

The support 110 comprises a seat 130 against which the object 150 is able to come to rest. In particular, the seat is that part of the support that accepts the upper part 160 of the object 150. In the example illustrated in FIGS. 1 to 6, the axis of the tube coincides with the axis of the passage passing through the seat.

According to one particular aspect, the seat 130 takes the form, with respect to the tube, of a radial shoulder which extends toward the longitudinal axis of the tube while leaving space to allow part of the object, in this example the screw body 170, to extend below the seat 130, while another part of the object, in this example the tulip 160, remains resting against the seat 130 and extends above said seat 130.

In other words, the seat 130 has an annular shape with a passage axis parallel to or coincident with the axis of the tube.

Advantageously, the seat 130 is surmounted by a top wall 140 which extends at least partially around the seat, delimiting a passage in the continuation of the passage delimited by the seat 130. The top wall 140 thus with the seat 130 delimits an insertion passage and a housing able to surround all or part of the tulip 160.

The internal face of the top wall 140 has a shape which, in collaboration with the external face of the tulip 160, is able to limit or block the rotation of the tulip 160 with respect to the support 110 and therefore with respect to the tube 100 about the longitudinal axis of the tube.

The rotation limiting or blocking function is achieved by the collaboration of shapes. To this end, the internal face of the top wall 140 comprises at least one planar part 146 (or flat) able to come to face a corresponding planar part 161 formed on the external face of the implant (see FIG. 3), particularly the external face of the tulip 160.

Figure 3:
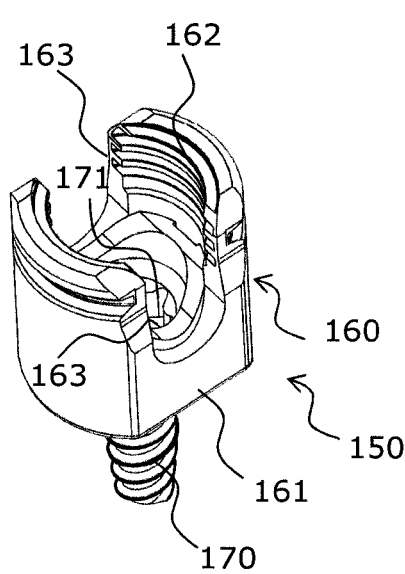
FIG. 3 is an isolated view of a medical implant for example in accordance with the medical implant of FIG. 2.

According to one particular aspect and as illustrated more particularly in FIGS. 2 to 4, the internal face of the top wall 140 of the support 110 comprises two opposed planar parts 146 intended to face two opposed planar parts 161 of the tulip.

The top wall 140 of the support 110 thus has two diametrically opposed openings 143 which open to the upper end of the top wall and define a reference for the orientation of the tulip 160 of the implant 150 with respect to the support 110 when it is being introduced into the support 110.

In particular, the opposing lateral openings 163 of the tulip 160 are intended to come to face corresponding openings 143 of the support to ensure that the planar parts 161 of the tulip 160 are indeed facing the corresponding planar parts 146 of the internal face of the top wall 140 of the support.

According to one particular aspect, at least one portion of the tube 100 has a cross section which decreases from the opening of the tube toward the bottom of the tube. In particular, provision may be made for the tube to have a frustoconical overall shape. Such a reduction in cross section makes it possible, in the case of an embodiment as illustrated in FIG. 5, to reduce the risk of the support being pushed to the bottom of the tube. The main hollow body of the other embodiments may also be of frustoconical overall shape.

The support 110 also comprises a bottom wall 120 which delimits an axial passage in the continuation of the axial passage delimited by the seat and by the top wall, and into which the screw 170 is able to extend in the state in which the tulip 160 is resting on the seat 130.

The bottom wall 120 of the support 110 has an opposite end 129 to the seat 130 which comes into contact with or the immediate vicinity of the bottom 109 of the tube. In particular, in the example illustrated in the figures, the bottom wall 130 comprises two diametrically opposite legs 121 which between them delimit the screw passage. These legs 121 continue as far as the bottom of the tube.

According to one particular aspect, the legs are flexible. The legs are configured so that when introduced into the main hollow body and the interior wall of the latter has a conical shape, the legs flex and tend to rub against the interior wall of the main hollow body, thus improving the axial retention of the support in the main hollow body. In contrast with the implant which is not axially wedged in position with respect to the support, the support is axially wedged with respect to the main hollow body in which it is housed.

Thus, when the operator pushes with his instrument against the object in order to grasp it, the corresponding thrusting force is absorbed by the support 110, the lower end 129 of which remains resting against the bottom 109 of the tube, thus preventing the object from dropping to the bottom of the tube.

The bottom wall 520, 620 of the support 510, 610 of the embodiment of FIG. 5 and of the embodiment of FIG. 6, which are introduced hereinafter, also makes it possible to prevent the implant from dropping to the bottom of the tube.

When the screw 170, which extends into the space delimited by the bottom wall 120, is able to move angularly in pivoting about an axis orthogonal to the longitudinal axis of the tube, the support 110 is configured to limit or block such angular travel.

This function of limiting or blocking angular travel may be obtained using an element which is coupled to the bottom wall and which is brought into contact with the lower part of the object.

Particularly in the example illustrated in FIG. 1, the device for this purpose comprises an element 180 which has fins for regulating the position of the element 180 along the opposing legs 121 that form the lower wall, until such point as the end of the screw 170 is engaged in the hollow part formed by the body of said element 180. The element 180 also allows the length of the screw 170 to be visualized or estimated.

The embodiment illustrated in FIG. 5 again shows the tube 100, the stopper 101 and houses a support 510 which, like in the other embodiments, is limited or blocked in terms of rotation with respect to the tube, for example by collaboration of shapes as described in respect of the example of FIG. 1.

The support 510 also comprises a seat and a top wall 540 which may repeat the features described hereinabove in respect of the example of FIG. 1. The support comprises a bottom wall 520 which differs from the bottom wall 120 in that it is shorter and remains distant from the bottom of the tube. Furthermore, the bottom wall 520 extends all around the axis of the support, whereas the bottom wall 120 in the example of FIG. 1 takes the form of two legs or tabs separated from one another. This then yields a bottom wall 520 which takes the form of a hollow cylinder of reduced height open at both ends.

In the example illustrated in FIG. 5, the medical implant reference 550 comprises a tulip 560 and a screw 570 which are longer than those of the implant 160. Of course, different sizes and/or shapes of implant can be used.

The support 510 also has a function of limiting or blocking the rotation of the tulip 560 of the implant 550 with respect to the support 510. This rotation limiting or blocking function can be obtained by collaboration of shapes as described hereinabove of the example of FIG. 1.

According to one embodiment, the function of limiting or blocking the angular travel of the screw is obtained by suitable dimensioning of the bottom wall which, according to one particular aspect, has a reduced diameter compared with the diameter of the top wall.

Thus, according to one particular aspect that can be applied to the other embodiments, the internal face of the bottom wall 520 is close to the screw 570 which extends facing the internal face of the bottom wall 520, namely closer to the axis of the tube than is the top wall 570.

According to one given embodiment illustrated in FIG. 5 and FIG. 5A, and which can be applied to the other embodiments, an element 590 is housed between the stopper and the object to block or limit the axial movement of the object along the tube toward the tube opening, namely toward the stopper. Of course, once the stopper and this element 590 have been removed, the object can be freely taken out of the tube using an instrument or by inclining the tube downward.

By virtue of the element 590 and of the support, the medical implant can thus be kept axially immobile whatever the position, for example inverted, of the tube, so long as the stopper has not been removed.

The embodiment illustrated in FIG. 6 again shows the tube 100, the stopper 101 and houses a support 610 which, as in the other embodiments, is limited or blocked in rotation with respect to the tube, for example by collaboration of shapes as described in respect of the example of FIG. 1. The medical implant is referenced 650 and comprises a tulip 660 and a screw 670 which may be similar or identical to the implant used in FIG. 5. Of course, other dimensions and/or shapes of implants can be used.

The support also has a function of limiting or blocking rotation of the tulip 660 of the implant 650. This rotation blocking or limiting function may be obtained in the way described hereinabove in respect of the example of FIG. 1. The support also comprises a seat and a top wall 640 which may repeat the features described hereinabove in respect of the example of FIG. 1. Just half 630A of the seat is visible in FIG. 6A.

The support 610 comprises a bottom wall 620 which is closed at the end that touches the bottom of the tube. According to one particular aspect, the bottom wall extends all around the longitudinal axis of the support. Advantageously, the bottom wall 620 has openings into which there extend tabs 622A, 622B that make it possible to limit or block the travel of the screw 670 as explained hereinafter.

In the example illustrated in FIGS. 6 and 6A, the support 620 comprises two half-shells 620A, 620B that can be assembled with one another using snap-fastening elements 690A, 690B. The two half-shells are preferably identical and have a plane of assembly that passes through the longitudinal axis of the support, which corresponds more or less to the axis of the tube when the support is in the state in which it is introduced inside the tube.

Such a preferred embodiment makes the support easier to manufacture by plastic injection molding. As an alternative, the support may be produced as a monobloc component.

According to one particular embodiment, the support advantageously comprises one or more tabs making it possible to limit or block the angular travel or tilting of the screw. The or each tab also allows the operator to identify the length of the screw.

Thus, each half-shell 620A, 620B comprises at least one tab 622A, 622B such that the support has two diametrically opposed longitudinal tabs. At least part 623A, 623B of the tab extends toward the longitudinal axis of the tube 600 to make it possible to limit or block the angular travel of the part of the object 650 which extends into the space delimited by the bottom wall 620.

The implant can be unpackaged and extracted from the packaging device as follows. The following steps are described with reference to FIG. 1 but also apply to the other embodiments.

The operator removes the stopper 101 to open the tube 100. Where present, the operator also removes the stop element 590 (as for example in the embodiment of FIG. 5) that allows the implant to be immobilized during transport. Advantageously, provision may be made for the stop element to be coupled to the stopper so that it comes away with the stopper when the latter is removed.

The operator may then introduce an instrument into the tube 100 to bring a coupling part of the instrument into contact with a corresponding part 160 of the object 150. The operator then turns the instrument or part of the instrument on itself (which means to say about the axis of the tube) so as to make the external thread of said part of the instrument collaborate with the tapped thread of the tulip. The function whereby the support is blocked or limited in its rotation with respect to the tube, and as is the tulip with respect to the support, allows the tulip and the support not to turn freely in the tube when the operator attempts to couple the instrument to the tulip. Once the instrument is coupled to the tulip of the implant, the operator can extract the implant by a simple axial movement of the implant using the instrument, the implant remaining freely axially movable in the direction of the opening of the tube out of the tube 100, of the instrument and of the object 150 coupled to the instrument.

As an alternative, the step of extracting the object can be performed simply and quickly by inclining the tube so as to orient the opening of the tube downward and thus cause the screw to slide freely out of the support and out of the tube.

In the embodiments illustrated in the figures, said support is attached to the inside of the main hollow body. As an alternative, said support may be formed of one piece with said main hollow body. In other words, the main hollow body and the support may be monobloc.

In the embodiment of FIGS. 7 and 7A, the packaging device comprises a main hollow body 700 which has the form of a case having an opening on the top. A lid 701 is connected, articulated by a hinge 702 which may or may not be frangible, to the edge of the upper opening of the case 700. The case has a longitudinal axis A700.

The lid 701 is depicted in the open position that may of course adopt a closed position in which it prevents access to the inside of the case 700. When the lid 701 is in the closed position, a sealing strip may be applied to the slot defined between the edges of the lid 701 and of the case 700 which face one another, as described in application WO2014188142 A1 or else in application WO2018078242A1, notably by applying the sealing strip to the hinge, then along the slot and returning to the hinge.

The packaging device also comprises a support 710 housed inside the case 700.

The support 710 comprises a seat 730 which is able to accept the upper part 860 of the object 850, for example a tulip as in the example illustrated in the figures, and which has an axial through-passage to allow another part 840 of the object, smaller in diameter than the upper part 860 of the object, for example a screw body 870 as in the example illustrated in the figures, to pass axially through the seat 730 and extend below the seat 730, while the upper part 860 of the object, in this example the tulip, remains resting against the seat 730. The tulip extends above said seat 730. The tulip is surrounded over part of its height by a wall 740 of the support which extends the seat.

In other words, the seat 730 has an annular shape with a passage axis parallel to or coincident with the longitudinal axis of the case.

According to one particular aspect, the support 710 is fully housed in the case 700. Said support 710 is configured to accept the object 850. According to one particular aspect, the support 710 also comprises a place 740' to accept another object 950, such as a fastener having an external thread able to collaborate with a tapped thread formed in the tulip 860. This fastener is usually referred to as a screw or locking nut or else a "end cap". The place 740' may comprise a bottom which accepts the object 950 and a wall which surrounds the object at least in part. Said locking nut or screw may be held in its housing or place for example by wedging or by collaboration between its external thread with a tapped thread of the housing, while at the same time allowing said locking nut or screw to be extracted using an instrument.

The support 710 may have a height-measuring element, such as a rule 790, which extends below the level of the seat of the support so as to allow the length of the lower part of the object, in this instance the length of the screw body that remains visible, to be determined quickly. Specifically, according to one particular aspect, the main hollow body, in this instance a case, is made of a transparent material. In particular, the support has a suitable shape, notably under its seat, to allow the user to see the length of the part of the object that extends through the seat.

Said support 710 notably makes it possible to keep the object 850 suspended away from the bottom of the case. As illustrated in FIG. 7, the support may comprise a base 722, possibly fitted with feet 723, able to collaborate with corresponding housings made in the bottom of the case.

The support 710 has a transverse part, for example a plate 711, in the overall shape of a rectangle with rounded edges, which extends for example substantially at the height of the seat 730 and which forms a means for limiting or blocking the rotation of the support 710 inside the case 700 which is of a similar cross section. Any potential rotational movement of the support with respect to the case about the axis A730 of the passage passing through the seat 730 (or about another parallel axis) would cause the plate 711 to come into abutment against the interior peripheral wall of the case 700, thereby limiting or preventing the rotation of the support 710.

The support 710 may also have a bottom wall 720 which for example comprises legs 721 separated from one another and which extend below the seat and which, for preference, connect the plate 711 to the base 722. The legs may be bowed outward and flexible so as to rub against the inside of the case.

The support 710 may thus be configured in such a way as to limit or prevent it from leaving the case axially, making it possible, if the object or objects or some of the objects need to be released by inclining the case 700 with the lid 701 in the open state, for the object or objects to slide axially out of the case 700 while the support 710 remains in position in the case. This functionality of limiting or preventing the support from coming out (by wedging or by friction) may also be applied to the supports of the other embodiments.

Advantageously, the seat 730 is surmounted by a top wall 740 which extends at least partially around the seat, delimiting a passage in the continuation of the passage delimited by the seat 730. The top wall 740 thus with the seat 730 delimits an insertion passage and a housing able to surround all or part of the tulip 860.

FIG. 7A illustrates the fact that, like in the other embodiments, the upper part 860 (able to engage with an extraction instrument) of the object 850 is blocked from rotating with respect to the support 710 about the axis A730 of the passage passing through the corresponding seat. As with the other embodiments, provision may be made for it to be the shape of the top wall 740 which does not exhibit symmetry of revolution and which is able to come into contact with the part 860 in the event of a rotational movement, that forms an end stop limiting or preventing axial rotation of the part 860 of the object 850.

The internal face of the top wall 740 has a shape which, in collaboration with the external face of the tulip 860, makes it possible to limit or block the rotation of the tulip 860, with respect to the support 710 and therefore with respect to the case 700 about the axis A730 of the passage passing through the seat 730.

Provision may be made in particular for the features of the seat and/or of the top wall of the support of the embodiments of FIGS. 2 to 4 to be applicable to the seat and/or to the top wall of the embodiment of FIGS. 7 and 7A and 7B. The or each object that is suspended through the support may be the object, such as a pedicle screw, presented in the other embodiments.

As illustrated in FIG. 7B, provision may be made for several objects, such as pedicle screws, to be housed in the main hollow body, particularly when the latter takes the form of a case. In particular, provision may be made for the support to take the form of a set of two supports, which may or may not be joined to one another, formed together as a single piece or otherwise, and each having a seat able to accept the upper part of the corresponding object, the seat having an axial through-passage allowing the lower part of the object to pass through the seat. Said objects may be identical or otherwise, for example of different lengths. Each of the two supports of the set may have some or all of the features of the support of the embodiments set out hereinabove. In the example illustrated in FIG. 7B, each of the two supports also has a housing for the locking nut or screw.

It is also possible to make provision, as illustrated in FIG. 7B, for the set of supports to comprise retaining means 799 for retaining part of each object which extends under the corresponding seat of the support, for example hooks able to partially surround a screw body.

The main hollow body may be coupled (connected) to the closure element not by a screw thread but by some other means such as a hinge. A sealing strip may be applied along the edges of the stopper and hollow body which delimit their openings and which are able to face one another.

In the case of the use of a hinge, the strip may be applied along the slot that separates the stopper and the main hollow body (while remaining connected by the hinge). The strip may then be applied initially to the hinge, then applied to the opposing slot edges and returned to the hinge.

The invention is not restricted to the embodiments illustrated in the drawings. Accordingly, it must be understood that, when the features mentioned in the attached claims are followed by reference signs, these signs are included solely with a view to improving the understanding of the claims and are not in any way limiting of the scope of the claims.

In addition, the term "comprising" does not exclude other elements or steps. Furthermore, features or steps which are described with reference to one of the embodiments set out hereinabove may also be used in combination with other features or steps from other embodiments set out hereinabove.

The invention claimed is:

1. A device for packaging an object, comprising:
   a main hollow body, such as a tube or a case, the main hollow body having a first extremity that is closed and a second extremity opposed the first extremity which has an opening that is closable with a closure element,
   said closure element being able with respect to the main hollow body to exhibit a closed configuration in which access to the opening of the second extremity of the main hollow body is limited or prevented, and an open configuration in which access to the opening of the second extremity of the main hollow body is free,
   wherein the packaging device also comprises a support distinct from said main hollow body and housed inside the main hollow body, said support being configured to accept an object, such as a medical implant;
   and in that the support comprises a seat having a through-passage, said through-passage being configured to allow part of the object to extend below the seat, while another part of the object remains resting on the seat,
   said packaging device being configured to limit or block the rotation of the support with respect to the main hollow body about the axis of the through-passage of the seat,
   and in that the support is configured to limit or block the rotation of at least part of the object about the axis of the through-passage of the seat even when said closure element is in the open configuration and that said another part of the object remains resting on the seat, the object being freely movable along the axis of the through-passage of the seat, to slide axially out of the support and out of the main hollow body through the opening of the second extremity of the main hollow body when the closure element is in the open configuration whilst the support remains housed in the main hollow body.

2. The device as claimed in claim 1, wherein the support comprises a top wall of which the internal face is configured in such a way as, in collaboration with the external face of the object, to limit or block the rotation of said at least part of the object about the axis of the through-passage of the seat.

3. The device as claimed in claim 2 wherein the support also comprises a bottom wall delimiting an axial passage in which part of said object is able to extend when said object is in a state in which it is resting on the seat.

4. The device as claimed in claim 3, wherein the bottom wall of the support has an opposite end to the seat which comes into contact with or the immediate vicinity of the bottom of the main hollow body.

5. The device as claimed in claim 3, wherein the support is configured to limit or block an angular movement of the part of the object which extends into the passage delimited by the bottom wall of the support.

6. The device as claimed in claim 1, wherein the external face of the support comprises at least one planar part facing a planar part of the internal face of the main hollow body so as to limit or block the rotation of the support with respect to the main hollow body about the axis of the through-passage of the seat.

7. The device as claimed in claim 1, wherein the packaging device comprises a retaining element which is housed between the closure element and the object so as to block or limit the sliding of the object toward the opening of the main hollow body.

8. The device as claimed in claim 1, wherein the bottom wall of the support comprises at least one tab, preferably two diametrically opposed longitudinal tabs, of which at least part extends toward the axis of the through-passage of the seat so as to make it possible to limit or block the angular travel of the part of the object that extends in the space delimited by the bottom wall.

9. The device as claimed in claim 1, wherein the support comprises two half-shells that can be assembled with one another by snap-fastening.

10. The device as claimed in claim 1, wherein the main hollow body is translucent or transparent.

11. The device as claimed in claim 1, wherein a top wall of the support has two diametrically opposed openings which define a reference for the orientation of the object with respect to the support when it is being introduced into the support.

12. An assembly comprising a packaging device as claimed in claim 1, and said object.

13. The assembly as claimed in claim 12, wherein said object comprises a body, preferably a hollow body, called a tulip, which has an external thread or a tapped thread, the tulip being configured in such a way as to allow, when the closure element is in the open state, the use of an instrument having a complementary part able to engage with the external thread or the tapped thread of the tulip so as to extract the object from the main hollow body.

14. The assembly as claimed in claim 13, wherein the object comprises a screw of which the head is coupled to the tulip with a ball-joint connection, or fixedly.

15. A method for extracting the object of an assembly as claimed in claim 12, said method comprising the following steps:
- opening the closure element so as to open the main hollow body;
- bringing a coupling part of an instrument into contact with a corresponding part of the object;
- coupling the instrument to the object by rotating the coupling part of the instrument about the axis of the through-passage of the seat;
- extracting the instrument and the object, coupled to the instrument, from the main hollow body.

* * * * *